United States Patent [19]

Trick

[11] 4,342,308
[45] Aug. 3, 1982

[54] PENILE ERECTILE SYSTEM

[75] Inventor: Robert E. Trick, Racine, Wis.

[73] Assignee: Medical Engineering Corporation, Racine, Wis.

[21] Appl. No.: 193,526

[22] Filed: Oct. 2, 1980

[51] Int. Cl.³ .............................................. A61F 5/00
[52] U.S. Cl. ...................................................... 128/79
[58] Field of Search ......... 128/1 R, 79, 344, DIG. 25; 92/40, 132; 60/593

[56] References Cited

U.S. PATENT DOCUMENTS

| | | | |
|---|---|---|---|
| 2,455,859 | 12/1948 | Foley | 128/346 |
| 3,073,348 | 1/1963 | Allen | 92/40 X |
| 3,237,604 | 3/1966 | Johmann | 120/42.3 |
| 3,419,008 | 12/1968 | Plishner | 128/346 |
| 3,810,701 | 5/1974 | Freccero et al. | 401/110 |
| 3,853,122 | 12/1974 | Strauch et al. | 128/79 |
| 3,954,102 | 5/1976 | Buuck | 128/79 |
| 4,009,711 | 3/1977 | Uson | 128/79 |
| 4,056,095 | 11/1977 | Rey et al. | 128/1 R |
| 4,066,073 | 1/1978 | Finney et al. | 128/79 |
| 4,201,202 | 5/1980 | Finney et al. | 128/79 |
| 4,222,377 | 9/1980 | Burton | 128/1 R |
| 4,224,934 | 9/1980 | Scott et al. | 128/79 |
| 4,256,093 | 3/1981 | Helms et al. | 128/1 R |

FOREIGN PATENT DOCUMENTS

WO80/00302 3/1980 PCT Int'l Appl. ................. 128/79

Primary Examiner—Dalton L. Truluck
Attorney, Agent, or Firm—Quarles & Brady

[57] ABSTRACT

An implantable system for correcting erectile impotence includes a flexible penile implant with a non-distensible fluid chamber, a single stroke pump and tubing connecting the pump to the non-distensible fluid chamber of the implant. The fluid chamber, tubing and pump are substantially filled with hydraulic fluid and the implant is inflated and made rigid by collapsing a normally expanded pumping chamber to forcibly transfer fluid from the pumping chamber into the non-distensible chamber of the implant.

2 Claims, 5 Drawing Figures

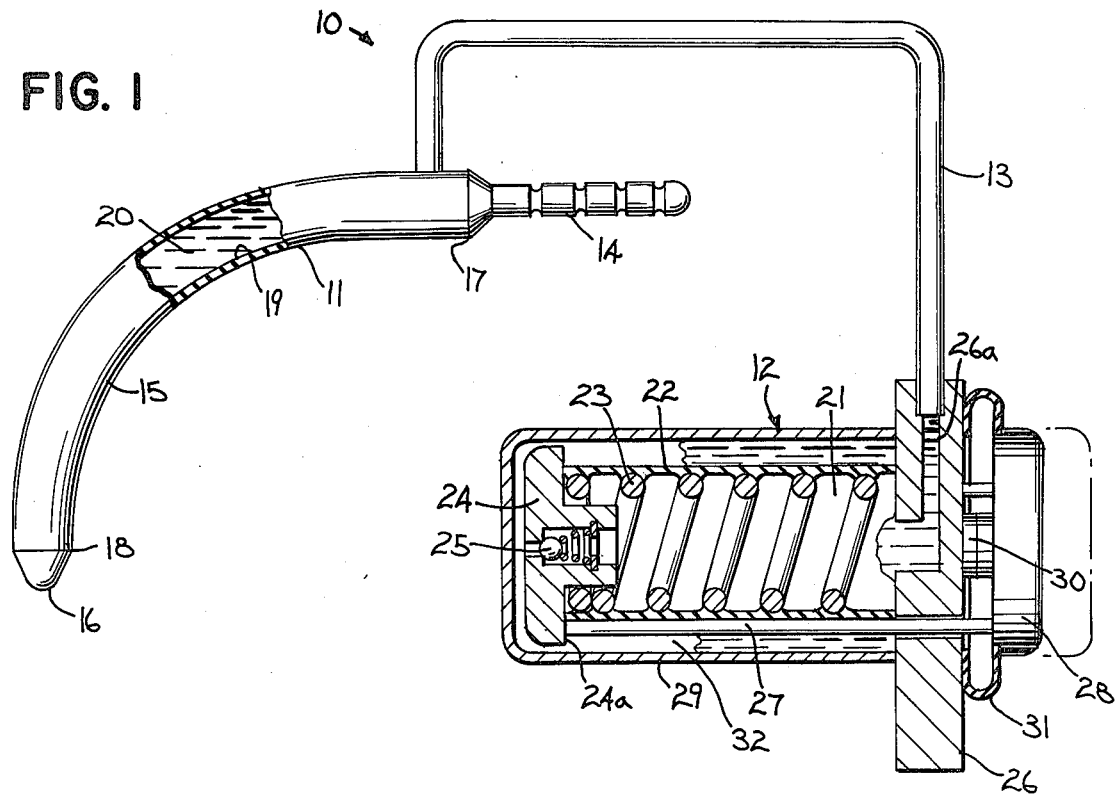
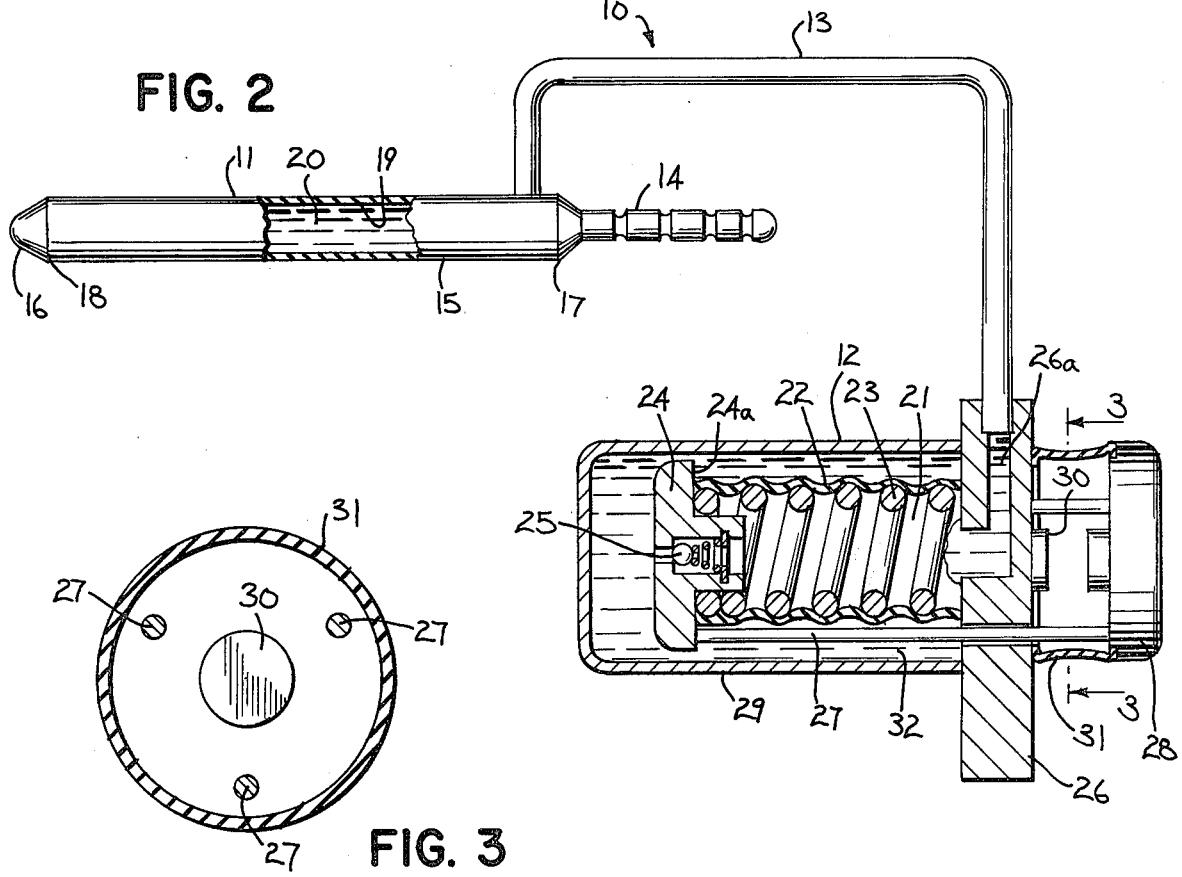

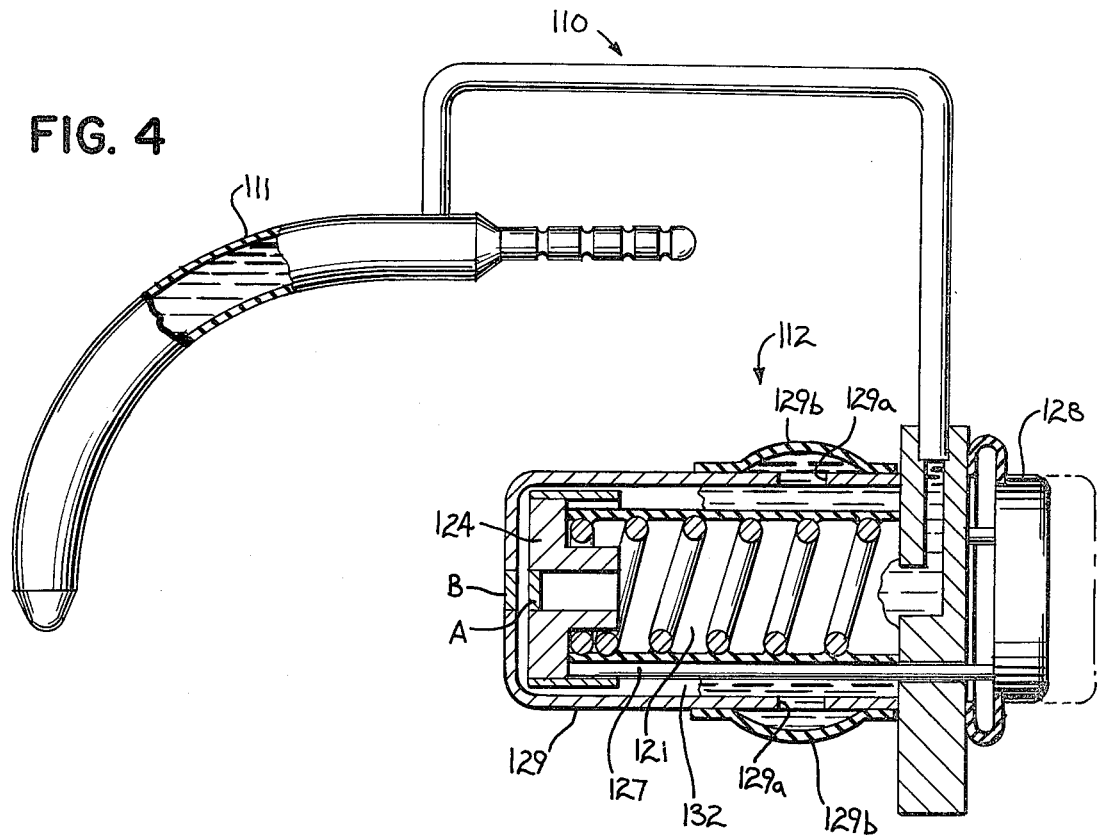
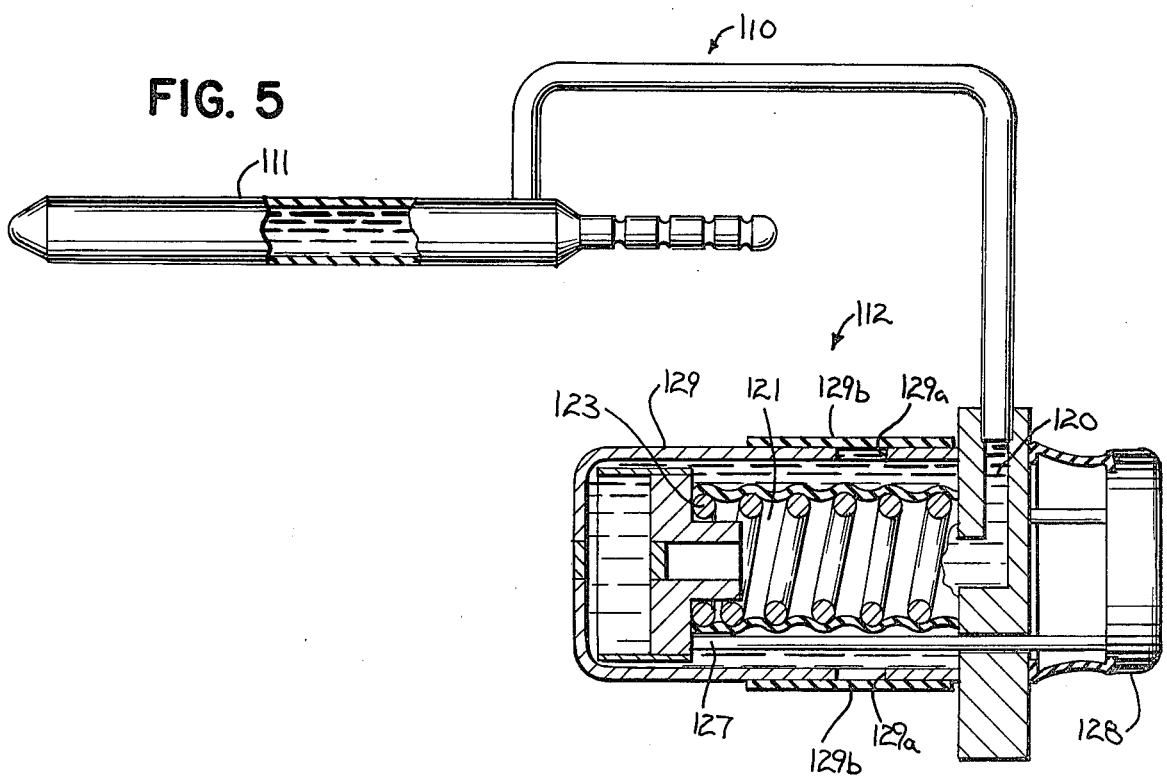

PENILE ERECTILE SYSTEM

The present invention relates to a penile erectile system. More particularly, it relates to an implantable penile erectile system which is useful in the treatment of erectile impotence.

BACKGROUND OF THE INVENTION

There are instances of erectile impotence in which the patient does not respond to more conventional therapy and the surgical implanting of a penile prosthesis may be the only practical means of remedying the impotency.

Several types of penile erectile systems have been employed in the past. One system comprises a pair of rods of suitable stiffness which are surgically implanted into the corpus cavernosum of the penis. One disadvantage of that type of system is that the permanent stiffness of the rod can be a source of physical pain and embarrassment, to the patient. The systems disclosed in U.S. Pat. No. 3,898,476 and U.S. Pat. No. 4,066,037 are representative of this type of system.

Another type of penile erectile system which is available is an inflatable system. The inflatable system normally includes two fairly long inflatable and distensible tubes that are surgically implanted in the corpus cavernosum of the penis. Each of the two tubes is connected by tubing to a pressure bulb of inflating fluid which is implanted elsewhere in the body. Because of the volume required to inflate, distend, pressurize and rigidize the distensible, inflatable tubes, the pressure bulbs are relatively large. The systems of U.S. Pat. No. 3,954,102 and U.S. Pat. No. 4,009,711 are representative of the available inflatable penile erectile systems.

SUMMARY OF THE INVENTION

It is the general object of the present invention to disclose a pressurizable penile erectile system.

The penile erectile system of the present invention includes a pair of hydraulically pressurizable, non-distensible penile implants, a unique pushbutton actuated single stroke pump which also serves as the hydraulic fluid reservoir and tubing which connects the pump to the implants to form a closed system which is substantially filled with hydraulic fluid.

Each of the implants of the system is a flexible, elongated member having a relatively short, proximal stem and an elongated flexible, distal portion having a conical tip and a non-distensible chamber.

The proximal stem of each of the implants is preferably solid and relatively stiff so that when it is implanted into the root end of the corpus cavernosum it will anchor and support the implant. The distal portion and tip of the implant are soft so as to cause a minimum of irritation to the tissue of the penis. The distal portion which contains the non-distensible chamber also is flexible so that when it is substantially filled with fluid but not pressurized the pendulus penis assumes a normal flaccid position. The tip of the distal portion of the implant is paraboloidal in shape to fit the end of the corpus cavernosum, and to enhance the physiological compatibility of the implant.

The push button actuated single stroke pump of the system of the present invention normally serves as the hydraulic fluid reservoir of the substantially filled system. The pump has a normally expanded collapsible pumping chamber which contains a spring which is biased towards collapsing the chamber. The spring is prevented from collapsing the pumping chamber by push rods which are held in place by the cooperation of an implanted permanent magnet and an iron push button. The push rods can be withdrawn from the pumping chamber by using an external magnet, which has a stronger attraction for the iron push button than the implanted magnet. When the push rods are withdrawn, the spring forcibly collapses the pumping chamber forcing hydraulic fluid under pressure through the connective tubing to completely fill and pressurize the non-distensible chambers of implants causing them to become rigid and the penis to stiffen. The pumping chamber is once again expanded and implants depressurized by moving the iron push button back in contact with the implanted magnet which places the push rods in position to overcome the bias of the spring.

In another embodiment, the pumping chamber is prevented from collapsing by push rods which are held in place by a catch and latch system which replaces the iron push button and magnet. The catch and latch system are actuated and released by depressing a push button.

Further objects and advantages of the present invention will become apparent from the drawings and the description of the preferred embodiment which follow:

BRIEF DESCRIPTION OF THE DRAWINGS

FIG. 1 is a side view, partly in section, of a first embodiment of the present invention in a non-pressurized condition;

FIG. 2 is a view similar to FIG. 1, except that the system is pressurized;

FIG. 3 is a view taken along the line 3—3 in FIG. 2.

FIG. 4 is a view similar to FIG. 1 of a second embodiment of the invention; and

FIG. 5 is a view similar to FIG. 4, except that the system is pressurized.

DESCRIPTION OF THE PREFERRED EMBODIMENTS

As seen in FIGS. 1 and 2 of the drawing, the first embodiment of the penile erectile system 10 includes a pair of identical elongated cylindrical penile implants 11 (only one of which is shown), a push button actuated pump 12 and tubing 13 connecting the implant 11 to the pump 12.

Still referring to FIG. 1, the implant 11 is seen to have a short, proximal stem 14 of relatively stiff material which is adapted to be implanted in the root end of the corpus cavernosum to support and anchor the implant, an intermediate tubular portion 15, and a conical distal tip 16. The tubular portion 15 and the tip 16 are of softer, flexible material as they are adapted to be implanted into the corpus cavernosum of the pendulus penis. The tip 16 is preferrably paraboloidal in shape to conform to the inner shape of the end of the corpus cavernosum.

The intermediate tubular portion 15 of the implant 11 is preferably formed of a silicone coated mesh or woven fabric which is nondistensible and will not stretch. It is sealed at its ends 17 and 18 to the stem 14 and tip 16, respectively, in a fluid-tight manner to form a cylindrical chamber 19. The seals 17 and 18 may be made with a suitable silicone adhesive or by other conventional means.

As seen in FIG. 1 even when the system 10 is not pressurized the chamber 19 is substantially filled with a non-compressible fluid 20, such as saline or a free flowing silicone gel, which prevents the chamber 19 from completely collapsing.

Referring specifically now to FIGS. 1 and 2, it can be seen that when the chamber 19 containing the non-compressible fluid 20 is completely filled with fluid under pressure, as in FIG. 2, it is rigid and when it is only substantially filled as in FIG. 1, the soft, flexible, nondistensible, intermediate tubular portion 15 of the implant 11 is flexible which permits the penis in which it is implanted to assume a substantially normal, flaccid position.

Still referring to FIGS. 1 and 2, it can be seen that the non-distensible chamber 19 of the implant 11 is joined by the length of connective tubing 13 to the pump 12. If a single pump 12 is to be used for a pair of implants 11 the tubing 13 will of necessity be forked or branched so that the pump 12 can deliver the hydraulic fluid 20 to the chamber 19 of each of the implants.

As seen in FIGS. 1 and 2, the pump 12 is enlarged to better show the details of its construction. As seen therein the pump 12 includes a collapsible cylindrical pumping chamber 21 which has a flexible wall 22 and contains a tension spring 23, which is preferably made of a biocompatible metal. The spring 23 is normally stretched and prevented from collapsing the chamber 21 as seen in FIG. 1.

The pumping chamber 21 has at one end an end cap 24 with a spring loaded ball check valve 25 and is attached at its other end to a mount 26. The spring 23 extends from the end cap 24 to the mount 26. The flexible wall 22, the end cap 24 and the mount 26 are joined in a fluid tight manner to form the pumping chamber 21. An internal passage 26a in the mount 26 connects the chamber 21 to the connective tubing 13.

As seen best in FIG. 1, the spring 23 which is attached to end cap 24 is biased toward pulling the end cap 24 towards the mount 26 to collapse and thereby reduce the effective volume of the chamber 21. The bias of the spring 23 is resisted by push rods 27. The push rods 27 are connected at one end to an iron push button 28 and the free ends of the push rods 27 extend into a protective cap 29 which surrounds the pumping chamber 21, to contact an external shoulder 24a of the end cap 24. The push rods 27 are retained in the position seen in FIG. 1, which is their normal position, by the magnetic attraction of a permanent magnet 30 for the iron push botton 28. The permanent magnet 30 is centrally mounted on the outside wall of the mount 26 as seen in FIG. 3.

As long as the push rods 27 are in the position seen in FIG. 1, the pumping chamber 21 is expanded and the nondistensible chamber 19 of the implant 11 is only substantially filled with the hydraulic fluid 20. However, when the magnetic attraction of the permanent magnet 30 for the iron push button 28 is overcome, preferably by use of an external magnet (not shown) the bias of the tension spring 23 forcibly moves the end cap 24 towards the mount 26 and hydraulic fluid 20 is forcibly displaced from the chamber 21 via the tubing 13 into the non-distensible chamber 19 of the implant 11 causing the implant 11 to become filled with fluid 20 under pressure and rigid as seen in FIG. 2.

The pump 12 is protected from attack by body fluids by the protective cap 29, the mount 26 and a flexible tubular membrane 31 which extends between the mount 26 and the push button 28 to form a fluid tight reservoir chamber 32. The reservoir chamber 32 is substantially filled at all times with hydraulic fluid 20 so that if any fluid 20 is lost from the pumping chamber 21 additional fluid 20 can enter the pumping chamber 21 through the check valve 25. The flexible membrane 31 in addition also serves to limit the extent to which the push button 28 can be moved away from the implanted magnet 30.

The term "substantially filled" as used herein to described the fluid content of the system means that the system contains about 60% to about 95% or more of its capacity of a non-compressible fluid such as water, saline or a free flowing gel. The actual content of fluid can vary; however, the distal portion of the implant when "substantially filled" should be still sufficiently flexible so that when it is implanted and not pressurized the pensi can assume a normal flaccid position.

All the parts and components of the prosthesis are preferably made of materials which are biocompatible or covered with medical grade silicone rubber which is nonreactive, non-toxic and well tolerated by the adjacent organic tissues. Silicone rubber is preferred, however, other suitable materials possessing desirable properties also can be employed.

The walls of the "non-distensible" chambers 19 are preferably made of a mesh or fabric covered with silicone material that will not stretch when filled with fluid so that excessive pressure will not be exerted on the tunica albuginea. The diameters of the sleeves are selected so that the implants fill the corpus cavernosum when they are in their pressurized state.

The proximal stem of the implant preferably has a Shore A hardness of about 70 and the distal tip a Shore A hardness of about 20. In addition, each of the materials has sufficient tensile strength for its intended use.

As previously described the chamber 19 of the implants 11 are pressurized by using an external magnet (not shown) to overcome the attraction of the permanent implanted magnet 30 for the iron push button 28 and to move the push button 28 outwardly thereby withdrawing the push rods 27 and permitting the spring 23 to forcibily collapse the chamber 21. The spring 23 is preferably calibrated to establish the ideal penile implant pressure. Abrupt deflections of low volume in the inplant will therefore cause only negligible pressure transients.

The penile implants 11 are deflated by manually pushing the push button 28 inwardly to move the push rods 27 which in turn moves the end cap 24 and stretches the spring 23 and expands the pumping chamber 21 thereby reducing the fluid pressure throughout the entire closed hydraulic system 10. When the pressure in the non-distensible chamber 19 of the penile implant 11 is relieved the distal portion of the implant becomes flexible and the penis flaccid.

Although in the foregoing discussion a single penile implant 11 has been described as being attached to the pump 12 it is possible because of the low volume of fluid 20 which is required to stiffen the already substantially filled non-distensible chamber 19 to operate two separate penile implants 11 with a single pump 12.

The penile implants 11 are preferably implanted through an incision made at the penoscrotal junction. After appropriate incision, the corpus cavernosum is dilated distally and proximally to accept the implants. The pump 12 is then implanted through a surgical incision in the scrotal wall and is positioned within the scrotum so that the push button 28 of the pump 12 is positioned subcutaneously and can be readily withdrawn from its normal position by use of an external magnet. Alternatively, if desired, the pump 12 can be implanted in the abdominal cavity of the patient.

In the second embodiment of the invention shown in FIGS. 4 and 5, the penile erectile system 110 is identical to the system 10 shown in FIGS. 1 to 3 except for the construction of the push button actuated single stroke pump 112.

The pump 112 of the second embodiment primarily differs from the pump 12 of the first embodiment in that in place of the permanent magnet 30 and the iron push button 28 it employs a latch/unlatch mechanism. Another difference in the second embodiment is that in place of the check valve 25 of the first embodiment, the end cap 124 of the pump 112 has septum A which is of resealable material and the protective cap 129 has a second septum B. The septums A and B are used to add fluid to the system 110. This is done by piercing the septums A and/or B with a syringe and needle (not shown) and injecting the fluid into the pumping chamber 121 or reservoir chamber 132 or both. Adjustments in the fluid level thus may be made at time of implantation or later if required.

The embodiment of FIGS. 4 and 5 also differs from the first embodiment in that a number of openings 129a extend through the wall of the cap 129. The openings 129a lead from the interior of the cap 129 into the interior of an inflatable elastic cuff 129b. As seen in FIG. 4, when the pushbutton 128 is depressed the cuff 129b is inflated by fluid displaced from the reservoir chamber 132. However, when the pushbutton 128 assumes the position seen in FIG. 5 there is room enough for the fluid in the reservoir chamber 132 and the cuff 129b deflates.

The latch and unlatch mechanism which is not shown in detail in FIGS. 4 and 5 can be a relatively simple one of the type used in ball point pens and the like. Suitable mechanisms are described in U.S. Pat. No. 3,237,604 and U.S. Pat. No. 3,810,701, the descriptions of which are incorporated by reference herein.

The embodiment of FIGS. 4 and 5 operates in the same manner as that of FIGS. 1 and 3. The pumping chamber 121 is normally expanded as shown in FIG. 4 and is held in that position by a latch/unlatch mechanism. When the push button 128 is depressed and released the latch/unlatch mechanism is disengaged and the push rods 127 are removed from their normal position holding the pumping chamber 121 expanded. As a result of the removal of the push rods 127, the spring 123 forcibly collapses the chamber 121 pumping the fluid 120 under pressure into the chamber 119 of the implant 111 filling it and causing it to become rigid as seen in FIG. 5. The system 100 is returned to its normal state seen in FIG. 4 by again pressing and releasing the push button 128 to engage the latch/unlatch mechanism.

It will be apparent to those skilled in the art that a number of modifications and changes may be made without departing from the spirit and scope of the present invention. For example, in place of a pair of implants the system may employ a single dual chambered inplant which fills both corpora. Therefore, it is intended that the invention not be limited except by the claims.

I claim:

1. A penile erectile system includes:
   (a) An elongated cylindrical penile inplant having a stem at one end, a conical tip at the other end, and a nondistensible chamber;
   (b) a single stroke pump for pressurizing the nondistensible chamber, said pump including:
      (i) an expanded collapsible pumping chamber,
      (ii) a removable rod which prevents the chamber from being collapsed and maintains said pumping chamber in a normal expanded condition, and
      (iii) means for collapsing the expandable pumping chamber to reduce its effective volume upon removal of said removable means and
   (c) tubing connecting the non-distensible chamber of; the implant and the pumping chamber so that when the pump, implant and tubing are substantially filled with hydraulic fluid and the pumping chamber is collapsed, hydraulic fluid is forcibly displaced under pressure through the tubing to completely fill, pressurize and make rigid the non-distensible chamber of the implant.

2. The system of claim 1 in which a ferrous metal push button is connected to one end of the removable rod and the system includes a permanent magnet which cooperates with the push button to keep the rod in position to prevent the pumping chamber from being collapsed.

* * * * *